United States Patent [19]
Ju et al.

[11] Patent Number: 5,948,690
[45] Date of Patent: Sep. 7, 1999

[54] PRETREATMENT SYSTEM FOR ANALYZING IMPURITIES CONTAINED IN FLAT SAMPLE

[75] Inventors: Jin-Ho Ju, Seoul; Sung-Chul Kang, Seongnam; Yong-Kyun Ko, Kyungki-do, all of Rep. of Korea

[73] Assignee: Samsung Electronics Co., Ltd., Suwon, Rep. of Korea

[21] Appl. No.: 08/768,704

[22] Filed: Dec. 18, 1996

[30] Foreign Application Priority Data

Dec. 21, 1995 [KR] Rep. of Korea ............... 95-53373

[51] Int. Cl.$^6$ ............ G01N 1/00; G01N 31/00; B65D 85/00
[52] U.S. Cl. ............ 436/174; 422/104; 206/205; 206/710; 211/41.18; 438/15; 438/115; 438/142; 438/450
[58] Field of Search ............ 422/99, 100, 102, 422/104; 435/288.3, 303.1; 436/174, 177, 171; 359/395, 398; 206/205, 710, 711, 712; 211/41.18; 414/935; 438/FOR 450, FOR 142, 963, 115, 15

[56] References Cited

U.S. PATENT DOCUMENTS 4,886,162  12/1989  Ambrogio .
5,284,802  2/1994  Muraoka et al. .

FOREIGN PATENT DOCUMENTS 6-249770  9/1994  Japan .

*Primary Examiner*—Elizabeth McKane
*Attorney, Agent, or Firm*—Jones & Volentine, L.L.P.

[57] ABSTRACT

A pretreatment system for analyzing impurities contained in a flat sample contains a cylindrical lower case having a stepped portion on which the flat sample is seated. The stepped portion is formed in an circumferential inner surface of the cylindrical lower case. A cylindrical upper case is detachably attached to an upper surface of the lower case, and has a supply passage through which a predetermined amount of pretreatment solution can be supplied to the flat sample. A cover closes off the upper surface of the upper case.

14 Claims, 3 Drawing Sheets

PRETREATMENT SYSTEM FOR ANALYZING IMPURITIES CONTAINED IN FLAT SAMPLE

BACKGROUND OF THE INVENTION

1. Field of the Invention

The present invention relates to a pretreatment system for analyzing impurities contained in a flat sample, and more particularly, to a pretreatment system for analyzing impurities contained in a flat sample where a pretreatment solution is applied on, for example, the surface of a wafer for semiconductor manufacturing, or a glass for a liquid crystal display, to dissolve impurities and thereby to easily analyze and estimate metal contamination and ion contamination.

2. Description of the Related Art

Generally, in semiconductor manufacturing processes, detecting wafer contamination is crucial to increase productivity and to control contamination levels. Although particle contamination can be identified by a high intensity light or an electronic microscope, metal contamination or ion contamination formed on the surface of a wafer can by identified by a pretreatment process.

In the conventional pretreatment process, as shown in FIG. 1, a pretreatment solution such as distilled water, HF, $H_2O_2$, or $HNO_3$, etc. is first dropped onto the surface of a sample 10, such as a flat wafer or a glass for a liquid crystal display, and then the surface is scanned in the direction of an arrow as shown in FIG. 1. Then, the pretreatment solution having impurities absorbed and dissolved therein is collected, and the contamination level is analyzed by an atomic absorption spectrometer or a high performance ion chromatography.

The pretreatment process of the prior art can analyze contamination levels to some extent in certain situations, such as when the sample is a wafer made from pure silicon and the wafer has not passed through an integrated circuit forming process. However, when a integrated circuit, etc. is formed on the wafer, or a layer such as polycrystalline silicon, $Si_3N_4$, etc. is deposited onto the surface of the wafer, it is very difficult not only to scan the surface of the sample, but also to determine the proper amount of the pretreatment solution to be supplied to the sample. This is because the amount of pretreatment solution varies with changes in surface conditions, such as hydrophilic properties. Accordingly, the amount of the collected pretreatment solution is changed each time, thereby making it difficult to implement quantitative analysis. Furthermore, when the pretreatment solution is held for a long time to sufficiently dissolve the impurities in the pretreatment solution, the pretreatment solution is apt to become contaminated due to surrounding environmental conditions.

SUMMARY OF THE INVENTION

Accordingly, the present invention has made in an effort to solve one or more of the problems occurring in the prior art, and it is an object of the present invention to provide a pretreatment system for analyzing impurities contained in a flat sample, in which a constant amount of pretreatment solution is supplied to the surface of a flat sample, which is placed in an enclosed space, so that a scanning process is not necessary and the amount of collected pretreatment solution is made constant, whereby quantitative analysis can be easily performed.

It is another object of the present invention to provide a pretreatment system for analyzing impurities contained in a flat sample, which can prevent foreign substances from flowing into the sample and the pretreatment solution, so that the sample does not become contaminated.

According to one aspect of the present invention, there is provided a pretreatment system for analyzing impurities contained in a flat sample, comprising: a cylindrical lower case having a central opening defining a lower circumferential inner surface; a stepped portion, formed in the lower circumferential inner surface of the cylindrical lower case, on which the flat sample is seated; a cylindrical upper case, having a central opening defining an upper circumferential inner surface, the cylindrical upper case being detachably attached to an upper surface of the lower case and having a supply passage through which a predetermined amount of pretreatment solution can be supplied to the flat sample; and a cover detachably attached to an upper surface of the cylindrical upper case for closing off the cylindrical upper case.

According to another aspect of the present invention, the lower and upper cases are made from polytetrafluoroethylene resin.

According to another aspect of the present invention, the supply passage is formed on the upper and inner circumferential surfaces of the upper case. According to still another aspect of the present invention, the supply passage is formed to have a diverging width toward the sample so that the pretreatment solution can easily flow toward the sample.

According to yet still another aspect of the present invention, the lower surface of the cover is formed to define an inclined surface which is downwardly projected in a center portion thereof.

By the features of the present invention, since it is possible to supply a constant amount of pretreatment solution to the surface of a flat sample, a scanning process is not necessary and the amount of collected pretreatment solution is made constant, whereby quantitative analysis can be easily performed. Also, foreign substances are prevented from flowing into the sample and the pretreatment solution, so that the sample does not become contaminated.

BRIEF DESCRIPTION OF THE DRAWINGS

The above objects, and other features and advantages of the present invention will become more apparent after a reading of the following detailed description taken in conjunction with the drawings, in which.

DETAILED DESCRIPTION OF PREFERRED EMBODIMENT

Figure 1:
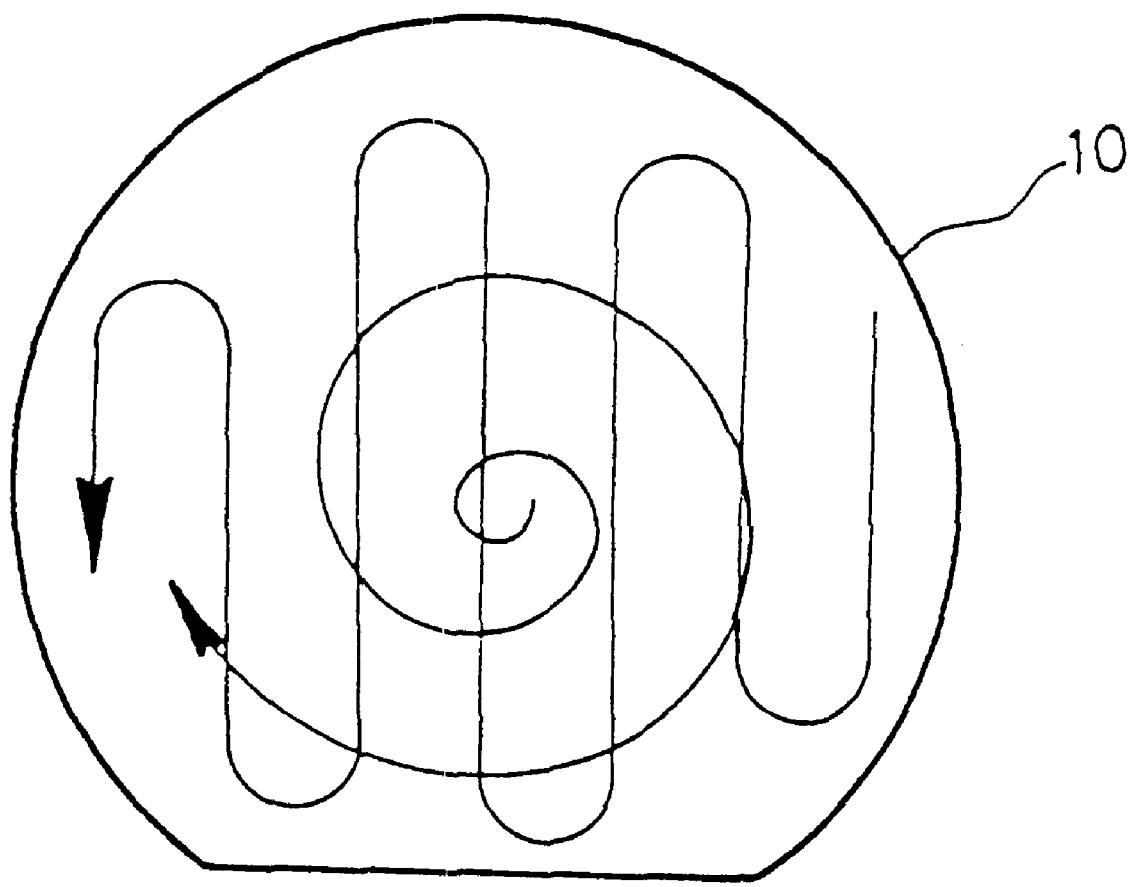
FIG. 1 is a plan view illustrating a conventional pretreatment process for analyzing impurities contained in a flat sample.
Figure 2:
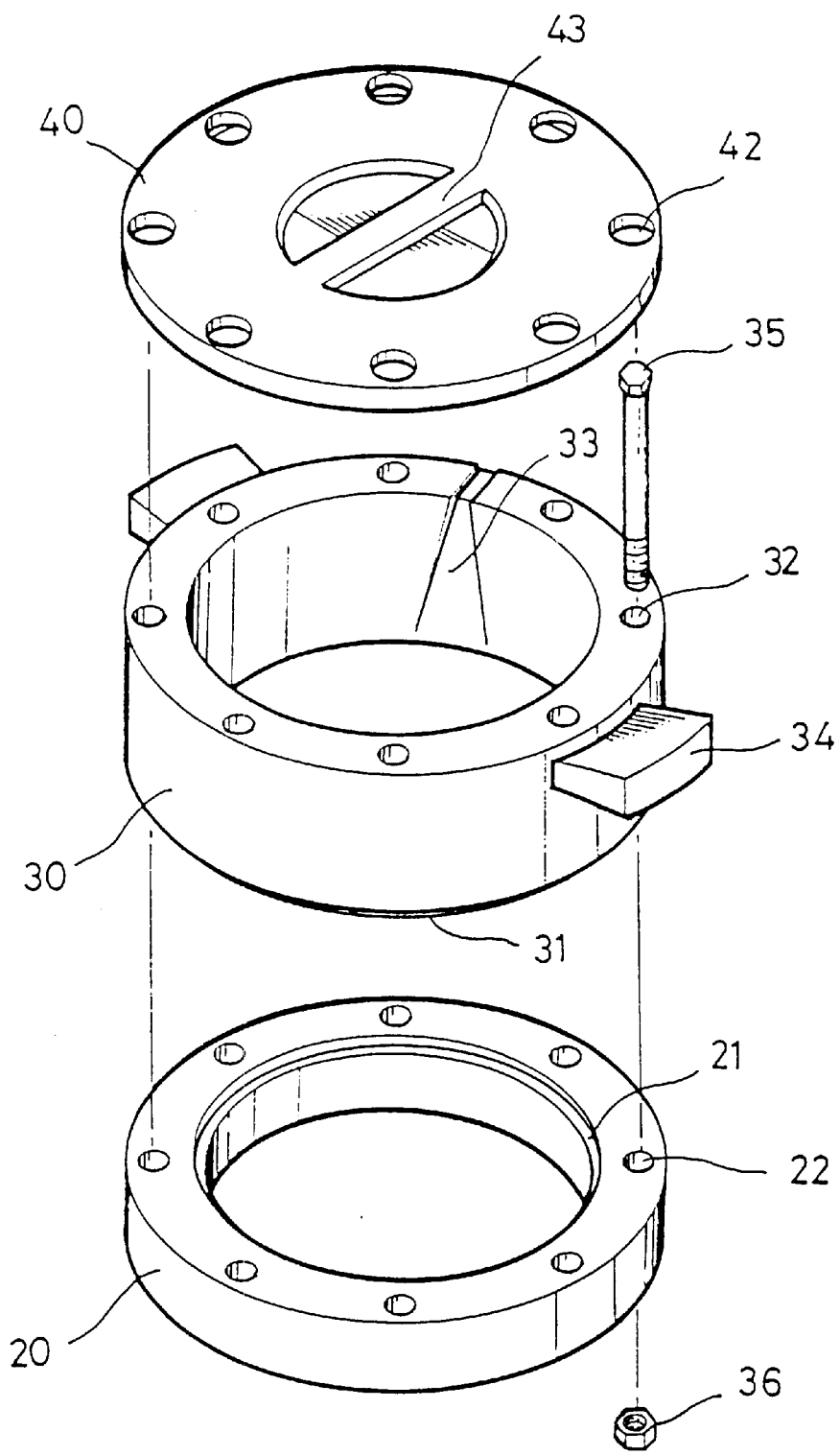
FIG. 2 is an exploded perspective view illustrating a pretreatment system for analyzing impurities contained in a flat sample, in accordance with an embodiment of the present invention.
Figure 3:
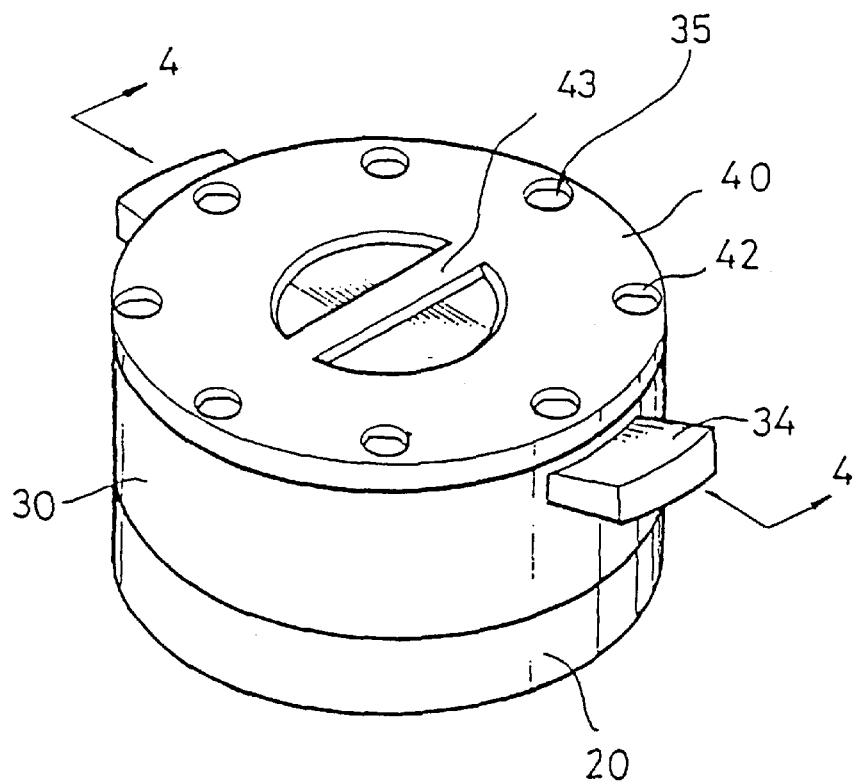
FIG. 3 is a perspective view illustrating the pretreatment system of FIG. 2, which is in an assembled state.
Figure 4:
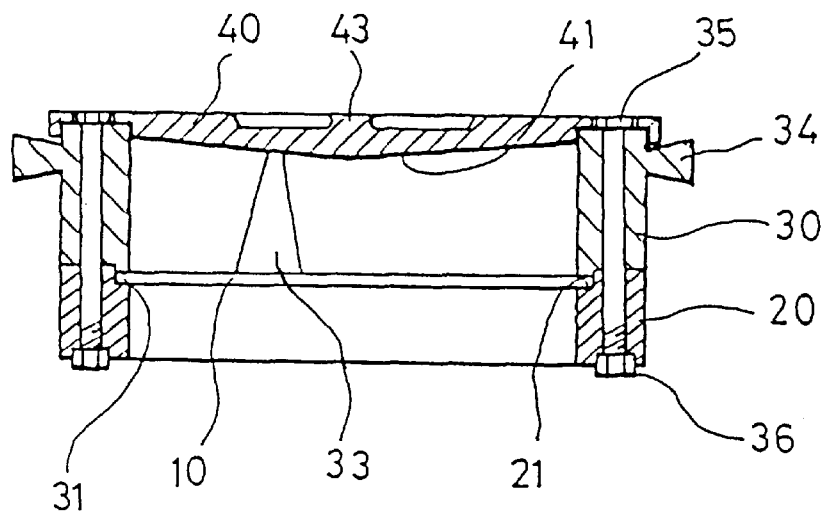
FIG. 4 is a cross-sectional view taken along the line 4—4 of FIG. 3.

Hereinafter, a pretreatment system for analyzing impurities contained in a flat sample in accordance with an embodiment of the present invention will be described in greater detail with reference to FIGS. 2 through 4.

In the drawings, the pretreatment system of the present invention includes a lower case 20, an upper case 30 and a cover 40. Each of the lower case 20 and the upper case 30 is formed with a central opening defining an inner circumferential surface. A stepped portion 21 is formed in the circumferential inner surface of the lower case 20, and a flat sample 10, such as a wafer or a glass for a liquid crystal display, is seated on the stepped portion 21. A first plurality of through holes 22 are formed in the body of the lower case 20 to axially extend therealong, the first plurality of through holes 22 being spaced apart from each other.

The upper case 30 is coupled to the upper surface of the lower case 20 to fixedly maintain the sample 10 seated on the stepped portion 21. A reversed stepped portion 31 is formed in the circumferential inner surface of the upper case 30, which contacts the upper surface of the sample 10. A second plurality of through holes 32 are formed in the body of the upper case 30 to axially extend therealong, the second plurality of through holes 32 being spaced apart from each other and in alignment with the first plurality of through holes 22.

On the upper surface and the circumferential inner surface of the upper case 30, there is defined a supplying passage 33 through which a pretreatment solution can be supplied from the outside. Specifically, as shown in FIG. 2, the supplying passage 33 has a first portion formed on the upper surface of the upper case and a second portion formed on the circumferential inner surface of the upper case. Preferably, the second portion of the supplying passage 33 is formed to have a diverging width toward the sample 10 so that the pretreatment solution can flow easily toward the sample 10 and be dispersed onto the sample 10. It is preferable that the pretreatment solution supplied through the supplying passage 33 be selected from a group consisting of HF of 1 weight %, HF of 5 weight %, $H_2O_2$ of 5 weight %, and $HNO_3$ of 5 weight %.

The lower case 20 and the upper case 30 are coupled to each other by a plurality of bolts 35 passing through the through holes 22 and 32 and a plurality of nuts 36 locked to ends of the plurality of bolts 35. To the circumferential outer surface of the upper case 30, there are secured a pair of handles 34 in an opposed manner to ensure that the pretreatment system of the present invention can be easily moved.

The cover 40 is disposed on the upper surface of the upper case 30 to close the upper portion of the upper case 30. The lower surface of the cover 40 is formed to define an inclined surface 41 which is downwardly projected in the center portion thereof. Adjacent the edge of the cover 40, there are formed a third plurality of through holes 42 through which the plurality of bolts 35 can be inserted, respectively. On the center portion of the upper surface of the cover 40 a grip 43 is provided.

It is preferable that the lower case 20, the upper cases 30 and the cover 40 are made from polytetrafluoroethylene resin to ensure durability and exhibit anti-chemical properties.

The operation of the pretreatment system for analyzing impurities contained in a flat sample, constructed as mentioned above, will be fully described hereinafter.

After the lower case 20, upper case 30, cover 40, bolts 35 and nuts 36 are cleaned by using a cleaning solution, these components are rinsed by overflowing a distilled water for more than 3 hours. Then, the lower case 20 and upper case 30 are dried in a purified nitrogen gas. The flat sample 10, such as a wafer for semiconductor manufacturing or a glass for a liquid crystal display, is seated on the stepped portion 21 of the lower case 20, and the upper case 30 is coupled to the upper surface of the lower case 20. By this, the reversed stepped portion 31 of the upper case 30 is contacted with the upper surface of the flat sample 10 seated on the stepped portion 21 of the lower case 20 to fixedly hold the flat sample 10. By passing the plurality of bolts 35 through the through holes 22 and 32 and locking the plurality of nuts 36 onto the ends of the plurality of bolts 35, the lower case 20 and the upper case 30 are securely coupled to each other. Then, a predetermined amount of the pretreatment solution is supplied onto the upper surface of the sample 10 through the supplying passage 33 formed on the upper case 30, and then the cover 40 is positioned onto the upper surface of the upper case 30 to maintain the sample 10 in an enclosed space. As mentioned above, it is preferable that the pretreatment solution supplied through the supplying passage 33 be selected from a group consisting of HF of 1 weight %, HF of 5 weight %, $H_2O_2$ of 5 weight %, and $HNO_3$ of 5 weight %.

After the predetermined amount of the pretreatment solution is supplied onto the upper surface of the sample 10, into which the impurities are dissolved, the contamination level can be analyzed by using an atomic absorption spectrometer or a high performance ion chromatography. At this time, since the cover 40 is provided on the upper case 30, the sample 10 can be held in an enclosed state, by which the contamination of the sample 10 due to foreign substances, and volatilization of the pretreatment solution, can be effectively prevented.

As a result, the pretreatment system of the present invention, constructed as described above, provides certain advantages. Since it is possible to supply a constant amount of pretreatment solution to the surface of a flat sample, a scanning process is not necessary and the amount of collected pretreatment solution is made constant, whereby quantitative analysis can be easily performed. Also, foreign substances are prevented from flowing into the sample and the pretreatment solution, so that the sample does not become contaminated.

In the drawings and specification, there have been disclosed typical preferred embodiments of the invention and, although specific terms are employed, they are used in a generic and descriptive sense only and not for purposes of limitation, the scope of the invention being set forth in the following claims.

What is claimed is:

1. A pretreatment system for use in analyzing impurities contained in a flat sample, comprising:

a cylindrical lower case having a lower circumferential inner surface defining a central opening, and an upper surface, said lower circumferential inner surface having a stepped portion forming a seat on which a flat sample is to be seated;

a cylindrical upper case having an upper outer surface, an upper circumferential inner surface defining a central opening, said cylindrical upper case being detachably attached to said cylindrical lower case in abutment with said upper surface of said lower case, and having a supply passage through which a predetermined amount of pretreatment solution can be supplied to a flat sample seated on said seat, said supply passage extending between said outer and said inner surfaces of said upper case and said supply passage having a width that increases in a direction toward said seat so that pretreatment solution can flow easily toward a flat sample seated on the seat; and a cover detachably attached to an upper surface of said cylindrical upper case so as to be movable between an open position and a closed position at which the cover blocks said opening and closes off the central opening of said cylindrical upper case from the outside of the upper case.

2. A pretreatment system for use in analyzing impurities contained in a flat sample as claimed in claim 1, wherein said cylindrical lower and upper cases are of a polytetrafluoroethylene resin.

3. A pretreatment system for use in analyzing impurities contained in a flat sample as claimed in claim 1, wherein the upper inner circumferential surface of said cylindrical upper case has a reversed stepped portion for contacting a flat sample seated on the seat to fixedly hold the flat sample.

4. A pretreatment system for use in analyzing impurities contained in a flat sample as claimed in claim 1, wherein said cylindrical upper case has an upper surface, and said supply passage has first and second potions, the first portion of said supply passage extending in said upper surface of said cylindrical upper case between said outer and said inner surfaces of said upper case, and the second portion extending in said upper circumferential inner surface of said cylindrical upper case.

5. A pretreatment system for use in analyzing impurities contained in a flat sample as claimed in claim 4, wherein said width of said supply passage increases in said second portion of the supply passage.

6. A pretreatment system for use in analyzing impurities contained in a flat sample as claimed in claim 1, wherein said cover has a lower surface which inclines downwardly from a peripheral portion to a central portion thereof.

7. A pretreatment method of analyzing impurities contained in a flat sample, the method comprising:
   placing the flat sample on a seat of a stepped portion of a circumferential inner surface of a lower case;
   detachably attaching a cylindrical upper case having a supply passage to an upper surface of said lower case;
   providing said supply passage with a width that increases in a direction toward said seat so that pretreatment solution can flow easily toward a flat sample seated on the seat;
   supplying a constant amount of pretreatment solution to a surface of the flat sample via the supply passage in the cylindrical upper case;
   closing said cylindrical upper case and blocking the opening in the upper case with a cover to prevent the pretreatment solution from evaporating into air flowing through the supply passage;
   allowing a predetermined amount of time to pass such that impurities contained on the surface of the flat sample dissolve into the pretreatment solution; and
   collecting and analyzing the pretreatment solution to determine a contamination level of the pretreatment solution.

8. A pretreatment method of analyzing impurities contained in a flat sample as claimed in claim 7, wherein the supplying comprises supplying pretreatment solution selected from the group consisting of HF of 1 weight %, HF of 5 weight %, $H_2O_2$ of 5 weight %, and $HNO_3$ of 5 weight %.

9. A pretreatment system for use in analyzing impurities contained in a flat sample, comprising:
   a cylindrical lower case having a lower circumferential inner surface defining a central opening, and an upper surface, said lower circumferential inner surface having a stepped portion forming a seat on which a flat sample is to be seated;
   a cylindrical upper case having an upper outer surface, an upper circumferential inner surface defining a central opening, said cylindrical upper case being detachably attached to said cylindrical lower case in abutment with said upper surface of said lower case, and having a supply passage through which a predetermined amount of pretreatment solution can be supplied to a flat sample seated on said seat, said supply passage extending between said outer and said inner surfaces of said upper case; and
   a cover detachably attached to an upper surface of said cylindrical upper case so as to be movable between an open position and a closed position at which the cover blocks said opening and closes off the central opening of said cylindrical upper case from the outside of the upper case, said cover having a lower surface which inclines downwardly from a peripheral portion to a central portion thereof.

10. A pretreatment system for use in analyzing impurities contained in a flat sample as claimed in claim 9, wherein said supply passage has a width that increases in a direction toward said seat so that pretreatment solution can flow easily toward a flat sample seated on the seat.

11. A pretreatment system for use in analyzing impurities contained in a flat sample as claimed in claim 10, wherein said cylindrical upper case has an upper surface, and said supply passage has first and second potions, the first portion of said supply passage extending in said upper surface of said cylindrical upper case between said outer and said inner surfaces of said upper case, and the second portion extending in said upper circumferential inner surface of said cylindrical upper case.

12. A pretreatment system for use in analyzing impurities contained in a flat sample as claimed in claim 11, wherein said second portion of the supply passage has a width that increases in a direction toward said seat so that pretreatment solution can flow easily toward a sample seated on the seat.

13. A pretreatment system for use in analyzing impurities contained in a flat sample as claimed in claim 10, wherein the upper inner circumferential surface of said cylindrical upper case has a reversed stepped portion for contacting a flat sample seated on the seat to fixedly hold the flat sample.

14. A pretreatment method of analyzing impurities contained in a flat sample, the method comprising:
   placing the flat sample on a seat of a stepped portion of a circumferential inner surface of a lower case;
   detachably attaching a cylindrical upper case having a supply passage to an upper surface of said lower case;
   supplying a constant amount of pretreatment solution to a surface of the flat sample via the supply passage in the cylindrical upper case;
   providing a cover having a lower surface which inclines downwardly from a peripheral portion to a central portion thereof;
   closing said cylindrical upper case and blocking the opening in the upper case with the cover to prevent the pretreatment solution from evaporating into air flowing through the supply passage;
   allowing a predetermined amount of time to pass such that impurities contained on the surface of the flat sample dissolve into the pretreatment solution; and
   collecting and analyzing the pretreatment solution to determine a contamination level of the pretreatment solution.

* * * * *